(12) United States Patent
Fang et al.

(10) Patent No.: US 8,193,316 B2
(45) Date of Patent: Jun. 5, 2012

(54) TACI-FC FUSION PROTEINS, METHODS OF MAKING AND USES THEREOF

(76) Inventors: Jianmin Fang, Shandong Province (CN); Zheng Liu, Jiangsu (CN)

( * ) Notice: Subject to any disclaimer, the term of this patent is extended or adjusted under 35 U.S.C. 154(b) by 0 days.

(21) Appl. No.: 12/638,392

(22) Filed: Dec. 15, 2009

(65) Prior Publication Data
US 2010/0136008 A1 Jun. 3, 2010

Related U.S. Application Data

(63) Continuation-in-part of application No. PCT/CN2008/001162, filed on Jun. 16, 2008.

(30) Foreign Application Priority Data

Jun. 15, 2007 (CN) .......................... 2007 1 0111162

(51) Int. Cl.
*C07K 1/00* (2006.01)
*C07K 14/00* (2006.01)
*C07K 17/00* (2006.01)
(52) U.S. Cl. ....................................... 530/351; 530/350
(58) Field of Classification Search ........................ None
See application file for complete search history.

(56) References Cited

U.S. PATENT DOCUMENTS
2009/0209006 A1* 8/2009 Rixon et al. ................. 435/69.7

FOREIGN PATENT DOCUMENTS
WO WO 02/094852 A2 11/2002

OTHER PUBLICATIONS

Skolnick and Fetrow. From genes to protein structure and function: novel applications of computational approaches in the genomic era. Trends in BioTechnology, 2000. vol. 18, pp. 34-39.*
Burgess, Shaheen, Ravera, Jaye, Donohue, and Winkles. Possible dissociation of the heparin-binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Schneider, P., "The role of APRIL and BAFF in lymphocyte activation," *Current opinion in immunology*, Jun. 2005, pp. 282-289, vol. 17, Issue 3.
Seyler, T.M., et al., "BLyS and APRIL in rheumatoid arthritis," *Journal of Clinical Investigation*, Nov. 1, 2005, pp. 3083-3092, vol. 115, Issue 11.
Von Bülow, G., et al., "NF-AT Activation Induced by a MAL-Interacting Member of the Tumor Necrosis Factor Receptor Superfamily," *Science*, Oct. 3, 1997, vol. 278.
Wang, H., et al., "TACI-ligand interactions are required for T cell activation and collagen-induced arthritis in mice," *Nature Immunology*, Jul. 2001, pp. 632-637, vol. 2, No. 7.
Wu, Y., et al., "Tumor Necrosis Factor (TNF) Receptor Superfamily Member TACI Is a High Affinity Receptor for Family Members APRIL and BLyS," *Journal of Biological Chemistry*, Aug. 23, 2000, pp. 35478-35485, vol. 275, No. 45.

* cited by examiner

*Primary Examiner* — Anne M. Gussow
(74) *Attorney, Agent, or Firm* — Saliwanchik, Lloyd & Eisenschenk

(57) ABSTRACT

The subject invention relates generally to novel biologically active TACI-Fc fusion proteins that bind to BLyS and/or APRIL and uses thereof. The invention also relates to methods for recombinant production of homogeneous TACI-Fc fusion proteins on a large scale.

15 Claims, 6 Drawing Sheets

SEQUENCE LISTING

<160> NUMBER OF SEQ ID NOS: 26

<210> SEQ ID NO 1
<211> LENGTH: 293
<212> TYPE: PRT
<213> ORGANISM: Homo sapiens

<400> SEQUENCE: 1

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

```
Asn Leu Pro Pro Glu Leu Arg Arg Gln Arg Ser Gly Glu Val Glu Asn
            115                 120                 125
Asn Ser Asp Asn Ser Gly Arg Tyr Gln Gly Leu Glu His Arg Gly Ser
    130                 135                 140
Glu Ala Ser Pro Ala Leu Pro Gly Leu Lys Leu Ser Ala Asp Gln Val
145                 150                 155                 160
Ala Leu Val Tyr Ser Thr Leu Gly Leu Cys Leu Cys Ala Val Leu Cys
                165                 170                 175
Cys Phe Leu Val Ala Val Ala Cys Phe Leu Lys Lys Arg Gly Asp Pro
            180                 185                 190
Cys Ser Cys Gln Pro Arg Ser Arg Pro Arg Gln Ser Pro Ala Lys Ser
        195                 200                 205
Ser Gln Asp His Ala Met Glu Ala Gly Ser Pro Val Ser Thr Ser Pro
    210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
                245                 250                 255
Gly Arg Trp Gly Cys His Thr Arg Thr Thr Val Leu Gln Pro Cys Pro
            260                 265                 270
His Ile Pro Asp Ser Gly Leu Gly Ile Val Cys Val Pro Ala Gln Glu
        275                 280                 285
Gly Gly Pro Gly Ala
        290

<210> SEQ ID NO 2
<211> LENGTH: 323
<212> TYPE: PRT
<213> ORGANISM: Artificial Sequence
<220> FEATURE:
<223> OTHER INFORMATION: TACI-Fc fusion protein

<400> SEQUENCE: 2

Ser Arg Val Asp Gln Glu Glu Arg Phe Pro Gln Gly Leu Trp Thr Gly
1               5                   10                  15
Val Ala Met Arg Ser Cys Pro Glu Glu Gln Tyr Trp Asp Pro Leu Leu
            20                  25                  30
Gly Thr Cys Met Ser Cys Lys Thr Ile Cys Asn His Gln Ser Gln Arg
        35                  40                  45
Thr Cys Ala Ala Phe Cys Arg Ser Leu Ser Cys Arg Lys Glu Gln Gly
    50                  55                  60
Lys Phe Tyr Asp His Leu Leu Arg Asp Cys Ile Ser Cys Ala Ser Ile
65                  70                  75                  80
Cys Gly Gln His Pro Lys Gln Cys Ala Tyr Phe Cys Glu Asn Lys Leu
                85                  90                  95
Asp Lys Pro His Thr Cys Pro Leu Cys Pro Ala Pro Glu Leu Leu Gly
            100                 105                 110
Gly Pro Ser Val Phe Leu Phe Pro Pro Lys Pro Lys Asp Thr Leu Met
        115                 120                 125
Ile Ser Arg Thr Pro Glu Val Thr Cys Val Val Val Asp Val Ser His
    130                 135                 140
Glu Asp Pro Glu Val Lys Phe Asn Trp Tyr Val Asp Gly Val Glu Val
145                 150                 155                 160
His Asn Ala Lys Thr Lys Pro Arg Glu Glu Gln Tyr Asn Ser Thr Tyr
                165                 170                 175
Arg Val Val Ser Val Leu Thr Val Leu His Gln Asp Trp Leu Asn Gly
```

```
                    180                 185                 190
Lys Glu Tyr Lys Cys Lys Val Ser Asn Lys Ala Leu Pro Ala Pro Ile
                195                 200                 205
Glu Lys Thr Ile Ser Lys Ala Lys Gly Gln Pro Arg Glu Pro Gln Val
            210                 215                 220
Tyr Thr Leu Pro Pro Ser Arg Asp Glu Leu Thr Lys Asn Gln Val Ser
225                 230                 235                 240
Leu Thr Cys Leu Val Lys Gly Phe Tyr Pro Ser Asp Ile Ala Val Glu
                245                 250                 255
Trp Glu Ser Asn Gly Gln Pro Glu Asn Asn Tyr Lys Thr Pro Pro
                260                 265                 270
Val Leu Asp Ser Asp Gly Ser Phe Phe Leu Tyr Ser Lys Leu Thr Val
            275                 280                 285
Asp Lys Ser Arg Trp Gln Gln Gly Asn Val Phe Ser Cys Ser Val Met
        290                 295                 300
His Glu Ala Leu His Asn His Tyr Thr Gln Lys Ser Leu Ser Leu Ser
305                 310                 315                 320
Pro Gly Lys

<210> SEQ ID NO 3
<211> LENGTH: 333
<212> TYPE: PRT
<213> ORGANISM: Artificial Sequence
<220> FEATURE:
<223> OTHER INFORMATION: TACI-Fc fusion protein

<400> SEQUENCE: 3

Ser Arg Val Asp Gln Glu Glu Arg Phe Pro Gln Gly Leu Trp Thr Gly
1               5                   10                  15
Val Ala Met Arg Ser Cys Pro Glu Glu Gln Tyr Trp Asp Pro Leu Leu
                20                  25                  30
Gly Thr Cys Met Ser Cys Lys Thr Ile Cys Asn His Gln Ser Gln Arg
            35                  40                  45
Thr Cys Ala Ala Phe Cys Arg Ser Leu Ser Cys Arg Lys Glu Gln Gly
        50                  55                  60
Lys Phe Tyr Asp His Leu Leu Arg Asp Cys Ile Ser Cys Ala Ser Ile
65                  70                  75                  80
Cys Gly Gln His Pro Lys Gln Cys Ala Tyr Phe Cys Glu Asn Lys Leu
                85                  90                  95
Arg Ser Pro Val Asn Leu Pro Pro Glu Leu Asp Lys His Pro Thr Cys
            100                 105                 110
Pro Leu Cys Pro Ala Pro Glu Leu Leu Gly Gly Pro Ser Val Phe Leu
        115                 120                 125
Phe Pro Pro Lys Pro Lys Asp Thr Leu Met Ile Ser Arg Thr Pro Glu
130                 135                 140
Val Thr Cys Val Val Val Asp Val Ser His Glu Asp Pro Glu Val Lys
145                 150                 155                 160
Phe Asn Trp Tyr Val Asp Gly Val Glu Val His Asn Ala Lys Thr Lys
                165                 170                 175
Pro Arg Glu Glu Gln Tyr Asn Ser Thr Tyr Arg Val Val Ser Val Leu
            180                 185                 190
Thr Val Leu His Gln Asp Trp Leu Asn Gly Lys Glu Tyr Lys Cys Lys
        195                 200                 205
Val Ser Asn Lys Ala Leu Pro Ala Pro Ile Glu Lys Thr Ile Ser Lys
        210                 215                 220
```

```
Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Ala Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330
```

<210> SEQ ID NO 4
<211> LENGTH: 342
<212> TYPE: PRT
<213> ORGANISM: Artificial Sequence
<220> FEATURE:
<223> OTHER INFORMATION: TACI-Fc fusion protein

<400> SEQUENCE: 4

```
Ser Arg Val Asp Gln Glu Glu Arg Phe Pro Gln Gly Leu Trp Thr Gly
1               5                   10                  15

Val Ala Met Arg Ser Cys Pro Glu Glu Gln Tyr Trp Asp Pro Leu Leu
                20                  25                  30

Gly Thr Cys Met Ser Cys Lys Thr Ile Cys Asn His Gln Ser Gln Arg
            35                  40                  45

Thr Cys Ala Ala Phe Cys Arg Ser Leu Ser Cys Arg Lys Glu Gln Gly
    50                  55                  60

Lys Phe Tyr Asp His Leu Leu Arg Asp Cys Ile Ser Cys Ala Ser Ile
65                  70                  75                  80

Cys Gly Gln His Pro Lys Gln Cys Ala Tyr Phe Cys Glu Asn Lys Leu
                85                  90                  95

Arg Ser Pro Val Asn Leu Pro Pro Glu Leu Gly Gly Gly Gly Gly Gly
            100                 105                 110

Gly Gly Gly Asp Lys Pro His Thr Cys Pro Leu Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
    195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
                245                 250                 255

Gln Val Ser Leu Thr Cys Leu Val Lys Gly Phe Tyr Pro Ser Asp Ile
```

```
                  260                 265                 270
Ala Val Glu Trp Glu Ser Asn Gly Gln Pro Glu Asn Tyr Lys Ala
            275                 280                 285

Thr Pro Pro Val Leu Asp Ser Asp Gly Ser Phe Phe Leu Tyr Ser Lys
            290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 5
<211> LENGTH: 313
<212> TYPE: PRT
<213> ORGANISM: Artificial Sequence
<220> FEATURE:
<223> OTHER INFORMATION: TACI-Fc fusion protein

<400> SEQUENCE: 5

Ala Met Arg Ser Cys Pro Glu Glu Gln Tyr Trp Asp Pro Leu Leu Gly
1               5                   10                  15

Thr Cys Met Ser Cys Lys Thr Ile Cys Asn His Gln Ser Gln Arg Thr
            20                  25                  30

Cys Ala Ala Phe Cys Arg Ser Leu Ser Cys Arg Lys Glu Gln Gly Lys
        35                  40                  45

Phe Tyr Asp His Leu Leu Arg Asp Cys Ile Ser Cys Ala Ser Ile Cys
    50                  55                  60

Gly Gln His Pro Lys Gln Cys Ala Tyr Phe Cys Glu Asn Lys Leu Arg
65                  70                  75                  80

Ser Glu Pro Lys Ser Ser Asp Lys Pro His Thr Cys Pro Leu Cys Pro
                85                  90                  95

Ala Pro Glu Leu Leu Gly Gly Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
    130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
        195                 200                 205

Pro Arg Glu Pro Gln Val Tyr Thr Leu Pro Pro Ser Arg Asp Glu Leu
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Ala Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285
```

Phe Ser Cys Ser Val Met His Glu Ala Leu His Asn His Tyr Thr Gln
    290                 295                 300

Lys Ser Leu Ser Leu Ser Pro Gly Lys
305                 310

<210> SEQ ID NO 6
<211> LENGTH: 969
<212> TYPE: DNA
<213> ORGANISM: Artificial Sequence
<220> FEATURE:
<223> OTHER INFORMATION: TACI-Fc fusion DNA

<400> SEQUENCE: 6

| | | | | | |
|---|---|---|---|---|---|
| agccgtgtgg | accaggagga | gcgctttcca | cagggcctgt | ggacgggggt | ggctatgaga | 60 |
| tcctgccccg | aagagcagta | ctgggatcct | ctgctgggta | cctgcatgtc | ctgcaaaacc | 120 |
| atttgcaacc | atcagagcca | gcgcacctgt | gcagccttct | gcaggtcact | cagctgccgc | 180 |
| aaggagcaag | gcaagttcta | tgaccatctc | ctgagggact | gcatcagctg | tgcctccatc | 240 |
| tgtggacagc | accctaagca | atgtgcatac | ttctgtgaga | caagctcga | caaacctcac | 300 |
| acatgcccac | tgtgcccagc | acctgaactc | ctggggggac | cgtcagtctt | cctcttcccc | 360 |
| ccaaaaccca | aggacaccct | catgatctcc | cggacccctg | aggtcacatg | cgtggtggtg | 420 |
| gacgtgagcc | acgaagaccc | tgaggtcaag | ttcaactggt | acgtggacgg | cgtggaggtg | 480 |
| cataatgcca | agacaaagcc | gcgggaggag | cagtacaaca | gcacgtaccg | tgtggtcagc | 540 |
| gtcctcaccg | tcctgcacca | ggactggctg | aatggcaagg | agtacaagtg | caaggtctcc | 600 |
| aacaaagccc | tcccagcccc | catcgagaaa | accatctcca | aagccaaagg | gcagccccga | 660 |
| gaaccacagg | tgtacaccct | gcccccatcc | cgggatgagc | tgaccaagaa | ccaggtcagc | 720 |
| ctgacctgcc | tagtcaaagg | cttctatccc | agcgacatcg | ccgtggagtg | ggagagcaat | 780 |
| gggcagccgg | agaacaacta | caaggccacg | cctcccgtgc | tggactccga | cggctccttc | 840 |
| ttcctctaca | gcaagctcac | cgtggacaag | agcaggtggc | agcaggggaa | cgtcttctca | 900 |
| tgctccgtga | tgcatgaggc | tctgcacaac | cactacacgc | agaagagcct | ctccctgtct | 960 |
| ccgggtaaa | | | | | | 969 |

<210> SEQ ID NO 7
<211> LENGTH: 999
<212> TYPE: DNA
<213> ORGANISM: Artificial Sequence
<220> FEATURE:
<223> OTHER INFORMATION: TACI-Fc fusion DNA

<400> SEQUENCE: 7

| | | | | | |
|---|---|---|---|---|---|
| agccgtgtgg | accaggagga | gcgctttcca | cagggcctgt | ggacgggggt | ggctatgaga | 60 |
| tcctgccccg | aagagcagta | ctgggatcct | ctgctgggta | cctgcatgtc | ctgcaaaacc | 120 |
| atttgcaacc | atcagagcca | gcgcacctgt | gcagccttct | gcaggtcact | cagctgccgc | 180 |
| aaggagcaag | gcaagttcta | tgaccatctc | ctgagggact | gcatcagctg | tgcctccatc | 240 |
| tgtggacagc | accctaagca | atgtgcatac | ttctgtgaga | caagctcag | agcccagtg | 300 |
| aaccttccac | cagagctcga | caaacctcac | acatgcccac | tgtgcccagc | acctgaactc | 360 |
| ctgggggac | cgtcagtctt | cctcttcccc | ccaaaaccca | aggacaccct | catgatctcc | 420 |
| cggacccctg | aggtcacatg | cgtggtggtg | gacgtgagcc | acgaagaccc | tgaggtcaag | 480 |
| ttcaactggt | acgtggacgg | cgtggaggtg | cataatgcca | agacaaagcc | gcgggaggag | 540 |
| cagtacaaca | gcacgtaccg | tgtggtcagc | gtcctcaccg | tcctgcacca | ggactggctg | 600 |

```
aatggcaagg agtacaagtg caaggtctcc aacaaagccc tcccagcccc catcgagaaa      660
accatctcca agccaaagg gcagccccga gaaccacagg tgtacaccct gcccccatcc       720
cgggatgagc tgaccaagaa ccaggtcagc ctgacctgcc tagtcaaagg cttctatccc     780
agcgacatcg ccgtggagtg ggagagcaat gggcagccgg agaacaacta caaggccacg     840
cctcccgtgc tggactccga cggctccttc ttcctctaca gcaagctcac cgtggacaag     900
agcaggtggc agcaggggaa cgtcttctca tgctccgtga tgcatgaggc tctgcacaac     960
cactacacgc agaagagcct ctccctgtct ccgggtaaa                            999
```

```
<210> SEQ ID NO 8
<211> LENGTH: 1026
<212> TYPE: DNA
<213> ORGANISM: Artificial Sequence
<220> FEATURE:
<223> OTHER INFORMATION: TACI-Fc fusion DNA

<400> SEQUENCE: 8
agccgtgtgg accaggagga gcgctttcca cagggcctgt ggacgggggt ggctatgaga      60
tcctgccccg aagagcagta ctgggatcct ctgctgggta cctgcatgtc ctgcaaaacc    120
atttgcaacc atcagagcca gcgcacctgt gcagccttct gcaggtcact cagctgccgc    180
aaggagcaag gcaagttcta tgaccatctc ctgagggact gcatcagctg tgcctccatc    240
tgtggacagc accctaagca atgtgcatac ttctgtgaga acaagctcag gagcccagtg    300
aaccttccac cagagctcgg tggaggtgga ggtggaggtg gaggtgacaa acctcacaca    360
tgcccactgt gcccagcacc tgaactcctg ggggaccgt cagtcttcct cttccccccc     420
aaacccaagg acaccctcat gatctcccgg acccctgagg tcacatgcgt ggtggtggac    480
gtgagccacg aagaccctga ggtcaagttc aactggtacg tggacggcgt ggaggtgcat    540
aatgccaaga caaagccgcg ggaggagcag tacaacagca cgtaccgtgt ggtcagcgtc    600
ctcaccgtcc tgcaccagga ctggctgaat ggcaaggagt acaagtgcaa ggtctccaac    660
aaagccctcc cagcccccat cgagaaaacc atctccaaag ccaaagggca gccccgagaa    720
ccacaggtgt acaccctgcc cccatcccgg gatgagctga ccaagaacca ggtcagcctg    780
acctgcctag tcaaaggctt ctatcccagc gacatcgccg tggagtggga gagcaatggg    840
cagccggaga caactacaa ggccacgcct cccgtgctgg actccgacgg ctccttcttc     900
ctctacagca agctcaccgt ggacaagagc aggtggcagc aggggaacgt cttctcatgc    960
tccgtgatgc atgaggctct gcacaaccac tacacgcaga agagcctctc cctgtctccg   1020
ggtaaa                                                              1026
```

```
<210> SEQ ID NO 9
<211> LENGTH: 938
<212> TYPE: DNA
<213> ORGANISM: Artificial Sequence
<220> FEATURE:
<223> OTHER INFORMATION: TACI-Fc fusion DNA

<400> SEQUENCE: 9
gctatgagat cctgccccga agagcagtac tgggatcctc tgctgggtac ctgcatgtcc     60
tgcaaaacca tttgcaacca tcagagccag cgcacctgtc agccttctgc aggtcactca    120
gctgccgcaa ggagcaaggc aagttctatg accatctcct gagggactgc atcagctgtg    180
cctccatctg tggacagcac cctaagcaat gtgcatactt ctgtgagaac aagctcagga    240
gcgagcccaa atcttcagac aaacctcaca catgcccact gtgcccagca cctgaactcc    300
```

-continued

```
tgggggacc gtcagtcttc ctcttccccc caaaacccaa ggacaccctc atgatctccc    360 ggaccctga ggtcacatgc gtggtggtgg acgtgagcca cgaagaccct gaggtcaagt    420
tcaactggta cgtggacggc gtggaggtgc ataatgccaa gacaaagccg cgggaggagc    480
agtacaacag cacgtaccgt gtggtcagcg tcctcaccgt cctgcaccag gactggctga    540
atggcaagga gtacaagtgc aaggtctcca caaagccct cccagccccc atcgagaaaa    600
ccatctccaa agccaaaggg cagccccgag aaccacaggt gtacaccctg cccccatccc    660
gggatgagct gaccaagaac caggtcagcc tgacctgcct agtcaaaggc ttctatccca    720
gcgacatcgc cgtggagtgg gagagcaatg ggcagccgga gaacaactac aaggccacgc    780
ctcccgtgct ggactccgac ggctccttct cctctacag caagctcacc gtggacaaga    840
gcaggtggca gcagggaac gtcttctcat gctccgtgat gcatgaggct ctgcacaacc    900
actacacgca gaagagcctc tccctgtctc cgggtaaa                           938
```

```
<210> SEQ ID NO 10
<211> LENGTH: 21
<212> TYPE: DNA
<213> ORGANISM: Artificial Sequence
<220> FEATURE:
<223> OTHER INFORMATION: Forward Primer sequences for DNA encoding the
      T1 fusion protein

<400> SEQUENCE: 10
agccgtgtgg accaggagga g                                             21

<210> SEQ ID NO 11
<211> LENGTH: 23
<212> TYPE: DNA
<213> ORGANISM: Artificial Sequence
<220> FEATURE:
<223> OTHER INFORMATION: Reverse Primer sequences for DNA encoding the
      T1 fusion protein

<400> SEQUENCE: 11
gagcttgttc tcacagaagt atg                                           23

<210> SEQ ID NO 12
<211> LENGTH: 21
<212> TYPE: DNA
<213> ORGANISM: Artificial Sequence
<220> FEATURE:
<223> OTHER INFORMATION: Forward Primer sequences for DNA encoding the
      T2 fusion protein

<400> SEQUENCE: 12
agccgtgtgg accaggagga g                                             21

<210> SEQ ID NO 13
<211> LENGTH: 23
<212> TYPE: DNA
<213> ORGANISM: Artificial Sequence
<220> FEATURE:
<223> OTHER INFORMATION: Reverse Primer sequences for DNA encoding the
      T2 fusion protein

<400> SEQUENCE: 13
gagctctggt ggaaggttca ctg                                           23

<210> SEQ ID NO 14
<211> LENGTH: 21
<212> TYPE: DNA
<213> ORGANISM: Artificial Sequence
```

```
<220> FEATURE:
<223> OTHER INFORMATION: Forward Primer sequences for DNA encoding the
      T3 fusion protein

<400> SEQUENCE: 14
agccgtgtgg accaggagga g                                              21

<210> SEQ ID NO 15
<211> LENGTH: 57
<212> TYPE: DNA
<213> ORGANISM: Artificial Sequence
<220> FEATURE:
<223> OTHER INFORMATION: Reverse Primer sequences for DNA encoding the
      T3 fusion protein

<400> SEQUENCE: 15
acctccacct ccacctccac ctccaccgag ctctggtgga aggttcactg ggctcct       57

<210> SEQ ID NO 16
<211> LENGTH: 22
<212> TYPE: DNA
<213> ORGANISM: Artificial Sequence
<220> FEATURE:
<223> OTHER INFORMATION: Forward Primer sequence for DNA encoding the T4
      fusion protein

<400> SEQUENCE: 16
gctatgagat cctgccccga ag                                             22

<210> SEQ ID NO 17
<211> LENGTH: 20
<212> TYPE: DNA
<213> ORGANISM: Artificial Sequence
<220> FEATURE:
<223> OTHER INFORMATION: Reverse Primer sequence for DNA encoding the T4
      fusion protein

<400> SEQUENCE: 17
tgaagatttg ggctcgctcc                                                20

<210> SEQ ID NO 18
<211> LENGTH: 9
<212> TYPE: PRT
<213> ORGANISM: Artificial Sequence
<220> FEATURE:
<223> OTHER INFORMATION: Linker for TACI-Fc fusion protein

<400> SEQUENCE: 18

Gly Gly Gly Gly Gly Gly Gly Gly Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Linker moiety for fusion proteins

<400> SEQUENCE: 19

Glu Glu Glu Glu Glu Glu Glu Glu Glu
1               5

<210> SEQ ID NO 20
<211> LENGTH: 9
<212> TYPE: PRT
<213> ORGANISM: Artificial Sequence
<220> FEATURE:
<223> OTHER INFORMATION: Linker moiety for fusion proteins
```

<400> SEQUENCE: 20

Ser Ser Ser Ser Ser Ser Ser Ser Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Linker moiety for fusion proteins

<400> SEQUENCE: 21

Gly Gly Gly Gly Gly Cys Pro Pro Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Linker moiety for fusion proteins

<400> SEQUENCE: 22

Gly Gly Gly Gly Ser Ser Ser
1               5

<210> SEQ ID NO 23
<211> LENGTH: 13
<212> TYPE: PRT
<213> ORGANISM: Artificial Sequence
<220> FEATURE:
<223> OTHER INFORMATION: Linker moiety for fusion proteins

<400> SEQUENCE: 23

Ser Cys Val Pro Leu Met Arg Cys Gly Gly Cys Cys Asn
1               5                   10

<210> SEQ ID NO 24
<211> LENGTH: 14
<212> TYPE: PRT
<213> ORGANISM: Homo sapiens

<400> SEQUENCE: 24

Pro Ser Cys Val Pro Leu Met Arg Cys Gly Gly Cys Cys Asn
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Linker for fusion protein

<400> SEQUENCE: 25

Gly Asp Leu Ile Tyr Arg Asn Gln Lys
1               5

<210> SEQ ID NO 26
<211> LENGTH: 23
<212> TYPE: PRT
<213> ORGANISM: Artificial Sequence
<220> FEATURE:
<223> OTHER INFORMATION: Linker moiety for fusion proteins

```
<400> SEQUENCE: 26

Gly Gly Gly Gly Gly Gly Gly Gly Gly Pro Ser Cys Val Pro Leu Met
1               5                   10                  15

Arg Cys Gly Gly Cys Cys Asn
            20
```

TACI-FC FUSION PROTEINS, METHODS OF MAKING AND USES THEREOF

CROSS-REFERENCE TO RELATED APPLICATION(S)

The present application is a continuation-in-part application of International Application Number PCT/CN2008/001162, filed Jun. 16, 2008; which claims priority to Chinese Patent Application No. 200710111162.2, filed Jun. 15, 2007, which are hereby incorporated by reference herein in their entirety, including any figures, tables, nucleic acid sequences, and amino acid sequences.

TECHNICAL FIELD

The invention relates generally to novel TACI-Fc fusion proteins, methods of making, and uses thereof.

BACKGROUND OF THE INVENTION

The process of lymphocyte development and differentiation is tightly controlled by cytokines. B lymphocyte stimulating factors (BLyS, also called BAFF, TNSF13B, THANK, TALL-1, and zTNF4) and a proliferation-inducing ligand (APRIL) belong to the tumor necrosis factor (TNF) and tumor necrosis factor receptor (TNFR) superfamilies that play a critical role in the survival and death of immune cells (Schneider, 2005, Current opinion in immunology, 17:282-289; Seyler et al., 2005, The Journal of Clinical investigation, 115:3083-3092). They provide key signals for the development and proliferation of B lymphocytes and T lymphocytes. In addition, they suppress lymphocyte apoptosis and stimulate the production of immunoglobulins in the blood (Wang et al., 2001, Nature Immunology, 2:632-637).

The over-expression of BLyS and APRIL, however, are associated with many lymphoproliferative disorders, as well as immunodeficiency and autoimmune diseases. These conditions include, for example, chronic lymphocyte leukemia, multiple myeloma, B lymphocyte lymphoma, systemic lupus erythematosus (SLE), rheumatoid arthritis (RA), and sicca syndrome. Further, clinical studies have shown that the degree of BLyS and APRIL over-expression correlates to the severity of diseases.

BLyS and APRIL regulate immune responses through binding to their receptors on the cell surface. Their pro-survival function is mainly regulated through the binding of BLyS to BAFF-R and B cell maturation antigen (BCMA) and/or APRIL to BCMA.

In contrast, transmembrane activator and calcium modulator and cyclophilin ligand interactor (TACI) function at least in part as a negative regulator of BLyS and APRIL activity. TACI has an extracellular domain, a transmembrane domain and an intracellular domain, wherein the extracellular domain includes an amino terminal region, a cystein-rich region and a stalk region. Because the cystein-rich region has high affinity to both BLyS and APRIL, the expression of TACI inhibits the pro-survival signaling pathway by blocking the binding of BLyS and APRIL to BAFF-R and/or BCMA.

Pre-clinical studies have shown that TACI or TACI-fusion proteins are useful for treating or ameliorating pathological immune conditions such as lymphoproliferative disorders, and autoimmune diseases.

Proprotein convertase (PC) is a group of enzymes that cleave proteins at specific sites. For many secretory protein or peptides, PC cleavage is a part of normal protein post-translational modification process for protein maturation or activation. For other proteins or polypeptides, the existing of PC cleavage sites within protein sequences may cause undesired protein cleavage. When the TACI sequence is analyzed by using the proprotein convertase (PC) artificial neural network computer program, a number of PC cleavage sites can be identified. PC cleavage at various sites results in TACI proteins that are heterogeneous in size, structure, stability, and activity. This enzymatic cleavage process also generates unwanted protein products.

To address this problem, PCT/US2002/015910 provides a method for avoiding PC cleavage by constructing a TACI-Fc fusion protein having no amino terminal region and only part of the stalk region. However, it is reported that the TACI-Fc fusion protein with no amino terminal region exhibits significantly reduced biological activity (Wu et al., 2000, The Journal of Biological Chemistry, 275:35478-35485). Consequently, there remains a substantial need for improved TACI-Fc fusion proteins that not only possess high binding affinity to BLyS and/or APRIL, but also exhibit biological activity similar to the native TACI protein. In addition, a need exists for improved methods of recombinant production of TACI proteins that are capable of yielding homogeneous biologically-active TACI protein products with lot-to-lot consistency.

BRIEF SUMMARY OF THE INVENTION

The subject invention provides novel biologically-active TACI-Fc fusion proteins that bind to BLyS and/or APRIL. Pharmaceutical compositions comprising these TACI-Fc fusion proteins are also provided. The invention also provides methods for recombinant production of homogeneous TACI-Fc fusion proteins on a large scale with lot-to-lot consistency.

One aspect of the invention provides an improved TACI-Fc fusion protein, comprising i) a TACI polypeptide, having an amino terminal region, a cystein-rich region, and a stalk region; and ii) a Fc domain. In a specific embodiment, the TACI polypeptide is part of a human or animal TACI polypeptide sequence.

Advantageously, in a preferred embodiment, the TACI-Fc fusion protein of the subject invention is capable of binding to BLyS and/or APRIL with high affinity. In addition, it is biologically active and uncleaved by proprotein convertases during post-translational processing.

In preferred embodiments, the amino acid sequence of the fusion protein comprises a TACI polypeptide that consists of amino acids 13-119 of SEQ ID NO:1 or a fragment thereof that starts at any of the amino acids from 13 to 29 of SEQ ID NO:1, extends through, and terminates at, any of the amino acids from 105 to 119 of SEQ ID NO:1; and wherein the fragment binds to BLyS or APRIL or both.

In one embodiment, the fusion protein comprises a TACI polypeptide that consists of amino acids 13-108 of SEQ ID NO:1. In another specific embodiment, the fusion protein comprises a TACI polypeptide that consists of amino acids 13-118 of SEQ ID NO:1. The sequence may also comprise any sequence that starts with amino acid 13 of SEQ ID NO:1, extends through, and terminates at least at amino acid 105 of SEQ ID NO:1 up to amino acid 119 of SEQ ID NO:1. This portion of the TACI-Fc fusion protein is the TACI portion and is attached, optionally through a linker, to the Fc portion of the protein.

In one embodiment, the Fc domain is a native human or animal immunoglobulin. In a specific embodiment, the Fc domain is selected from the group consisting of IgG, IgM, IgD, IgE and IgA. In a further specific embodiment, the Fc domain is IgG1.

In one embodiment, the TACI-Fc fusion protein comprises a linker sequence that links the TACI polypeptide to the Fc domain. In a specific embodiment, the linker sequence is 9Gly.

Another aspect of the invention provides a polynucleotide sequence encoding the TACI-Fc fusion protein of the subject invention. In a specific embodiment, the polynucleotide sequence is cDNA.

Another aspect of the invention provides a vector carrying a polynucleotide sequence encoding the TACI-Fc fusion protein of the subject invention. In a specific embodiment, the vector is a plasmid having DNA that encodes dihydrofolate reductase (DHFR).

Another aspect of the subject invention provides a host cell containing a polynucleotide sequence encoding the TACI-Fc fusion protein of the subject invention. In a specific embodiment, the host cell is a CHO cell.

Another aspect of the present invention provides pharmaceutical compositions comprising the subject TACI-Fc fusion protein and a pharmaceutically acceptable carrier. In a preferred embodiment, the pharmaceutical composition is capable of blocking the binding of BLyS to BAFF-R, BLyS to BMCA and/or APRIL to BMCA. In addition, in a preferred embodiment, the subject pharmaceutical composition is useful for inhibiting the proliferation of lymphocytes, stimulating apoptosis of malignant lymphocytes, and/or preventing transplant rejection in a subject.

Another aspect of the invention provides a method for recombinant production of a TACI-Fc fusion protein on a large scale. In a specific embodiment, this method comprises:
  i) constructing a TACI DNA fragment that does not contain proprotein cleavage sites;
  ii) joining the TACI DNA fragment with a Fc DNA to obtain a TACI-Fc fusion DNA;
  iii) inserting the TACI-Fc fusion DNA into a plasmid;
  iv) transfecting host cells with the TACI-Fc fusion plasmid DNA,
  v) expressing TACI-Fc fusion proteins, and
  vi) recovering TACI-Fc fusion proteins.

Advantageously, the present method is capable of producing TACI-Fc fusion proteins as a homogeneous composition on a large scale with high productivity.

In preferred embodiments, the subject TACI-Fc fusion protein is useful for treating or ameliorating conditions associated with B cell malignancy, autoimmune diseases, immunodeficiency, and/or the proliferation of tumor cells in a subject.

Therapeutic uses of the subject TACI-Fc protein include but, are not limited to, treating or ameliorating one or more of rheumatoid arthritis, psoriatic arthritis, systemic lupus erythematosus, lymphocyte tumor, psoriasis, dermatitis, inflammatory bowel disease, asthma, Type-I diabetes, multiple organ injury syndrome, coronary artery disease, allergies, solid organ transplant rejections, immune complex nephritis, stiff-man syndrome, Sjogren syndrome, Hashimoto thyroiditis, polymyositis, scleroderma, Addison's disease, vitiligo, pernicious anemia, glomerulonephritis, pulmonary fibrosis, leucopenia, central nervous system (CNS) inflammatory disorders, chronic inflammatory responses, myasthenia gravis, Crohn's disease, end stage renal failure, TACI-positive lymphomas and leukemias, Chronic lymphocytic leukemia, B cell prolymphocytic leukemia, Waldenstrom macroglobulinemia, splenic marginal zone B-cell lymphoma, extranodal marginal zone B-cell lymphoma of MALT type, Nodal marginal zone B-cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt lymphoma/leukemia, and lymphomatoid granulomatosis.

BRIEF DESCRIPTION OF THE SEQUENCES

Figure 1:
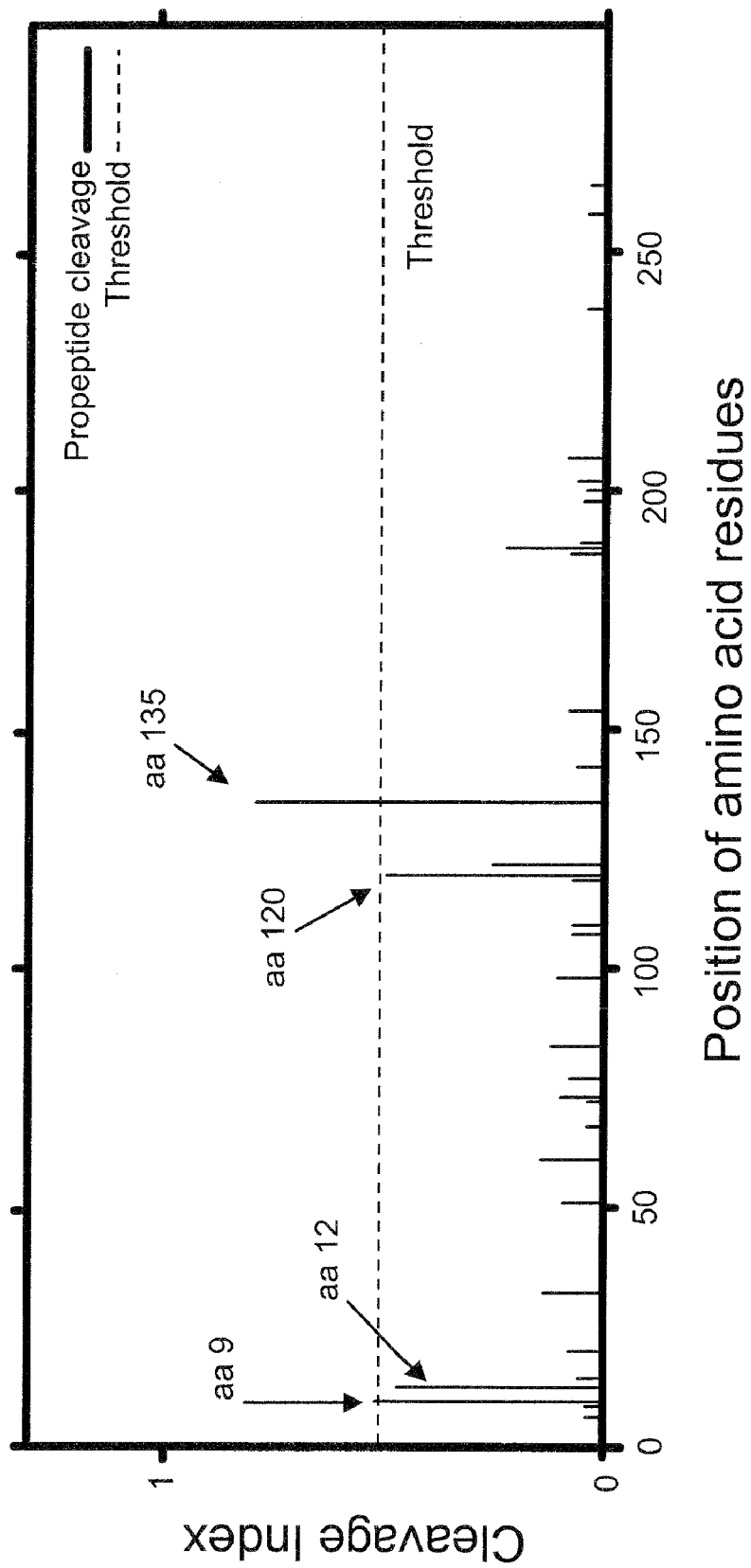
FIG. 1 is a schematic diagram depicting proprotein convertase cleavage sites of the native human TACI protein.

SEQ ID NO:1 is an amino acid sequence for the native human TACI protein.

SEQ ID NO:2 is an amino acid sequence for a TACI-Fc fusion protein of the subject invention (T1).

SEQ ID NO:3 is an amino acid sequence for a TACI-Fc fusion protein of the subject invention (T2).

SEQ ID NO:4 is an amino acid sequence for a TACI-Fc fusion protein of the subject invention (T3).

SEQ ID NO:5 is an amino acid sequence for a TACI-Fc fusion protein (T4).

SEQ ID NO:6 is a nucleic acid sequence encoding a TACI-Fc fusion protein of the subject invention (T1).

SEQ ID NO:7 is a nucleic acid sequence encoding a TACI-Fc fusion protein of the subject invention (T2).

SEQ ID NO:8 is a nucleic acid sequence encoding a TACI-Fc fusion protein of the subject invention (T3).

SEQ ID NO:9 is a nucleic acid sequence encoding a TACI-Fc fusion protein (T4).

SEQ ID NO:10 is a primer useful according to the subject invention.

SEQ ID NO:11 is a primer useful according to the subject invention.

SEQ ID NO:12 is a primer useful according to the subject invention.

SEQ ID NO:13 is a primer useful according to the subject invention.

SEQ ID NO:14 is a primer useful according to the subject invention.

SEQ ID NO:15 is a primer useful according to the subject invention.

SEQ ID NO:16 is a primer useful according to the subject invention.

SEQ ID NO:17 is a primer useful according to the subject invention.

SEQ ID NO:18 is an amino acid sequence of a linker of the subject invention.

SEQ ID NO:19 is an amino acid sequence of a linker of the subject invention.

SEQ ID NO:20 is an amino acid sequence of a linker of the subject invention.

SEQ ID NO:21 is an amino acid sequence of a linker of the subject invention.

SEQ ID NO:22 is an amino acid sequence of a linker of the subject invention.

SEQ ID NO:23 is an amino acid sequence of a linker of the subject invention.

SEQ ID NO:24 is an amino acid sequence of a linker of the subject invention.

SEQ ID NO:25 is an amino acid sequence of a linker of the subject invention.

SEQ ID NO:26 is an amino acid sequence of a linker of the subject invention.

DETAILED DISCLOSURE OF THE INVENTION

The subject invention provides improved TACI-Fc fusion proteins that bind to BLyS and/or APRIL. The subject invention further provides novel and advantageous methods for large-scale production of improved TACI-Fc fusion proteins.

In preferred embodiments, the subject fusion protein has high binding affinity to BLyS and/or APRIL, and is capable of inhibiting the pro-survival signaling pathway in immune cells by blocking the binding of BLyS and/or APRIL to BAFF-R and/or BCMA. In addition, in preferred embodiments, the subject biologically active fusion protein is not cleaved to a significant extent during post-translational processing in host cells, and hence, it is suitable for recombinant production of TACI-containing pharmaceutical composition on a large scale.

One aspect of the invention provides an improved TACI-Fc fusion protein that binds to BLyS and/or APRIL, comprising i) a TACI polypeptide, containing an amino terminal region, a cystein-rich region, and a stalk region; and ii) a Fc domain. In a specific embodiment, the TACI polypeptide is part of a human or animal TACI polypeptide.

In one embodiment, the amino acid sequence of the TACT portion of the fusion protein comprises a TACI polypeptide that consists of amino acids 13-119 of SEQ ID NO:1. In some embodiments, the amino acid sequence of the TACI portion of the fusion protein comprises a fragment that starts at any of the amino acids 13 to 29 of SEQ ID NO:1, extends through, and terminates at, any of the amino acids 105 to 119 of SEQ ID NO:1, wherein the fragment binds to BLyS or APRIL or both.

In certain specific embodiments, the amino acid sequence of the TACI portion of the fusion protein is a variant that has at least about 75%, more preferably at least about 85%, more preferably at least about 90%, more preferably at least about 95%, more preferably at least about 97%, and more preferably at least about 99% identity to a TACI polypeptide that consists of amino acids 13-119 of SEQ ID NO:1; or to a fragment that starts at any of the amino acids 13 to 29 of SEQ ID NO:1, extends through, and terminates at any of the amino acids 105 to 119 of SEQ ID NO:1, and wherein the fragment (and variant) binds to BLyS or APRIL or both.

The term "Fc domain" encompasses the full length and fragments of native human and animal Fc and Fc variant molecules and sequences, including for example IgG, IgM, IgD, IgE, IgA and subtypes such as for example IgG1, IgG2, IgG3, IgG4, IgA1, and IgA2. As with Fc variants and native Fc's, the term "Fc domain" includes molecules in monomeric or multimeric form, whether digested from whole antibody or produced by other means.

The term "Fc variant" refers to a molecule or sequence that is modified from a native Fc but still comprises a binding site for the salvage receptor. Fc domains include molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fe or by derivatizing (as defined below) such a native Fc.

The Fc domain within the scope of the invention can be of antibodies of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes. In a specific embodiment, the Fc domain is IgG1.

In another embodiment, the subject TACI-Fc fusion protein comprises a linker sequence that links the TACI polypeptide to the Fc domain. Linker would typically be a peptide chain. The length of the peptide may be, for example, 6, 7, 8, 9, 10, 11, 12, 13, 14, 15, 16, 17, 18, 19, 20, 21, 22, 23, 24, 25, 30, 40, 50 or more amino acid residues, but typically is between 5 and 25 residues. Depending upon the length and side chain composition, a linker may have, but need not have, greater than average flexibility. Flexibility can be calculated using algorithms known in the art. Preferably, the linker is not cleaved by proprotein convertase.

Linker sequences of the present invention can comprise, for example, 5-100 amino acid residues, 5-75 amino acid residues, 5-50 amino acid residues, 5-25 amino acid residues, 5-20 amino acid residues, 5-15 amino acid residues, 5-10 amino acid residues, or 5-9 amino acid residues. Examples of useful linkers include, but are not limited to, 9Gly (SEQ ID NO:18), 9Glu (SEQ ID NO:19), 9Ser (SEQ ID NO:20), 5GlyCys2ProCys (SEQ ID NO:21), 4Gly3Ser (SEQ ID NO:22), Ser Cys Val Pro Leu Met Arg Cys Gly Gly Cys Cys Asn (SEQ ID NO:23), Pro Ser Cys Val Pro Leu Met Arg Cys Gly Gly Cys Cys Asn (SEQ ID NO:24), Gly Asp Leu Ile Tyr Arg Asn Gln Lys (SEQ ID NO:25), and 9GlyProSerCysValProLeuMetArgCysGlyGlyCysCysAsn (SEQ ID NO:26).

In a specific embodiment, the linker sequence is 9Gly.

In a specific embodiment, the subject TACI-Fc fusion protein is T1 (SEQ ID. No:2).

In a specific embodiment, the subject TACI-Fc fusion protein is T2 (SEQ ID. No:3).

In a specific embodiment, the subject TACI-Fc fusion protein is T3 (SEQ ID. No:4).

The subject invention also embodies TACI-Fc fusion proteins that have undergone any of a variety of post-translational modification processes such as glycosylation.

Although the subject fusion protein eliminates potential PC cleavage sites in the amino terminal region and the stalk region of the TACI polypeptide, it does not remove the parts of the amino terminal region and the stalk region necessary for retaining substantially full biological activity. Therefore, in preferred embodiments, the subject fusion protein possesses biological activity similar to native human TACI proteins and is capable of blocking the proliferation of B-lymphocytes and stimulating apoptosis in malignant immune cells.

Further, the subject TACI-Fc fusion protein can be produced by site-directed mutagenesis that removes potential PC cleavage sites. Other similar methods can also be employed to yield the subject fusion protein.

In a preferred embodiment, the subject fusion protein binds specifically to BLyS, APRIL or both. "Specific binding" or "specificity" refers to the ability of a fusion protein or a fragment to detectably bind an epitope presented on a molecule, such as BLyS or APRIL, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

"Selectivity" refers to the preferential binding of a protein to a particular region, target, or peptide as opposed to one or more other biological molecules, structures, cells, tissues, etc. For example, selectivity can be determined by competitive ELISA or Biacore assays. The difference in affinity/avidity that marks selectivity can be any detectable preference (e.g., a ratio of more than 1:1.1, or more than about 1:5, if detectable).

As is well known in the art, individual amino acids can be encoded by different DNA sequences. Hence, the amino acid sequences of the subject fusion protein can be encoded by different DNA sequences; these DNA sequences fall within the scope of the present invention.

Furthermore, based on the common knowledge of TACI and antibody structure, some amino acids in a TACI-Fc fusion protein may be substituted, deleted, or added, without detracting from the biological activities of the fusion protein. In some cases, changes in the amino acid sequence of a protein may even improve the biological activities and/or improve certain properties compared to the original protein. In other cases, additional TACI-Fc fusion protein sequences may result from conservative and/or non-conservative modifications of the amino acid sequences of the aforementioned TACI polypeptide, the Fc domain, the linker sequence and fragments thereof. Conservative modifications will produce molecules having functional and chemical characteristics similar to those of the molecule from which such modifications are made. In addition, substantial modifications in the functional and/or chemical characteristics of the molecules may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule. Therefore, it is possible to modify the amino acid sequences of the subject TACI-Fc fusion protein to obtain fusion protein variants with similar, or even improved, biochemical or biological properties. These modified antibodies are within the scope of the present invention.

Desired amino acid substitutions (whether conservative or non-conservative) can be determined by those skilled in the art at the time such substitutions are desired. In certain embodiments, conservative amino acid substitutions also encompass non-naturally occurring amino acid residues which are typically incorporated by chemical peptide synthesis rather than by synthesis in biological systems.

A further aspect of the invention provides polynucleotide sequences encoding the subject TACI-Fc fusion protein. In a specific embodiment, the polynucleotide sequence is a cDNA.

In one embodiment, the DNA sequence (SEQ ID NO:6) encodes T1 (SEQ ID No:2).

In another embodiment, the DNA sequence (SEQ ID NO:7) encodes T2 (SEQ ID No:3).

In another embodiment, the DNA sequence (SEQ ID NO:8) encodes T3 (SEQ ID No:4).

Another aspect of the invention provides a vector carrying a polynucleotide sequence encoding a TACI-Fc fusion protein. The vector can be, for example, a plasmid or virus. In a specific embodiment, the vector is a plasmid that encodes dihydrofolate reductase (DHFR). In another specific embodiment, the vector is capable of being expressed in mammalian cells.

Another aspect of the invention provides a host cell containing a polynucleotide encoding the TACI-Fc fusion protein. The host cell can be a mammalian cell. In addition to mammalian cells, other expression systems may also be used, including but not limited to bacteria, yeasts and insect cells. Non-mammalian cells can result in a higher level of protein expression. However, non-mammalian cells may be incapable of producing glycosylated proteins or glycosylating proteins in a mammalian manner In one embodiment, host cells include mammalian cells such as for example CHO cells, SP20 cells, NSO cells, COS cells, BHK cells, and PerC6 cells. In a further specific embodiment, the host cell is a CHO cell.

Another aspect of the invention provides a pharmaceutical composition comprising the subject TACI-Fc fusion protein and a pharmaceutically acceptable carrier. In a preferred embodiment, the subject pharmaceutical composition is capable of blocking the binding of BLyS to BAFF-R, BLyS to BMCA and/or APRIL to BCMA. In addition, in preferred embodiments, the subject pharmaceutical composition is useful for inhibiting the proliferation of lymphocytes, stimulating apoptosis of malignant lymphocytes, and/or preventing transplant rejection in a subject.

Another aspect of the invention provides a method for producing a TACI-Fc fusion protein on a large scale, comprising:

i) constructing a TACI DNA fragment that does not contain proprotein cleavage sites;

ii) joining the TACI DNA fragment with a Fc DNA to obtain a TACI-Fc fusion DNA;

iii) inserting the TACI-Fc fusion DNA into a plasmid;

iv) transfecting host cells with the TACI-Fc fusion plasmid DNA, v) expressing TACI-Fc proteins, and vi) recovering TACI-Fc fusion proteins.

In one embodiment, the proprotein cleavage sites include the $9^{th}$ and the $135^{th}$ residues of the native human TACI polypeptide represented by SEQ ID No:1. In another embodiment, the proprotein cleavage sites further include the $12^{th}$ and the $120^{th}$ residues of the native human TACI polypeptide represented by SEQ ID No:1.

The TACI DNA fragment can be obtained by the following steps: i) extracting and purifying total RNA from human peripheral blood mononuclear cells; ii) reverse-transcribing mRNA to generate cDNA; and iii) amplifying TACI DNA by PCR.

In another embodiment, step ii) of the above method is: joining the TACT DNA fragment and the Fc domain using a linker sequence. In a specific embodiment, the linker sequence is 9Gly.

In one embodiment, TACI-Fc fusion proteins are recovered by extracting TACI-Fc proteins from the host cells and purifying TACI-fusion proteins.

Production of the TACI-Fc Fusion Protein

After obtaining TACI-Fc fusion DNA, TACI-Fc fusion proteins can be produced on a large scale by recombinant techniques. The TACI-Fc fusion DNA sequences can be inserted into a suitable vector. A signal peptide sequence is preferably present at the amino terminus of the fusion proteins to enable proper secretion. Specifically exemplified herein is the use of a plasmid as a vector. However, other vectors, such as viruses and DNA fragments, can also be used to express or produce this fusion protein.

In the vector, the fusion DNA open reading frames are located downstream of a promoter. A promoter drives transcription of mRNA from the fusion DNA open reading frames that include a start codon and a stop codon. The fusion DNA open reading frames can be constructed within a single vector, but they can also be inserted into two independent vectors. The vector may include DNA encoding an antibiotic resistance gene to facilitate plasmid replication in bacteria. In addition, the vector may also include a eukaryotic cell selection gene for selection of a stable cell line following transfection.

The vector that encodes fusion protein DNA sequences can be introduced into host cells, which then express the subject fusion protein. Various types of cells can be used as host cells. However, because the fusion proteins contain amino acid residues requiring glycosylation, mammalian cells are the ideal host cells because they provide glycosylation similar to the native TACI proteins. Among the most commonly used mammalian cells are Chinese hamster ovary (CHO) cells, mouse myeloma, and HEK293 cells. In addition, many other mammalian cells can also be used to express the subject fusion protein and are also included in this invention as host cells for the production of the subject fusion protein.

Furthermore, non-mammalian cells may also be used to express or produce the fusion protein of the subject invention. The non-mammalian cells may be eukaryotic cells, including but not limited to plant cells, insect cells, and yeast cells. The non-mammalian cells may also be prokaryotic cells, including but not limited to bacteria and fungi.

The methods that introduce the vector encoding the fusion protein into host cells include those widely used in molecular biology. For plasmid transfection, the most commonly used methods are electroporation and liposome-based transfection. Electroporation is specifically exemplified herein but other methods can also be used for the same purpose.

In addition to the preferred cell culture approach, other methods can also be used to produce the fusion protein of the subject invention. For example, as is well-known in the art, the fusion protein may be expressed in the organs of transgenic animals, such as in mammalian glands, muscles, or eggs. Moreover, the fusion protein can also be expressed in transgenic plants, such as the leaves of a transgenic plant, etc.

The subject invention also provides an initial step for the purification of this fusion protein from cell culture supernatants. The purified fusion protein can be properly formulated to become a fusion protein drug.

Determination of Levels of Protein Expression

Levels of protein expression can be determined by ELISA. Cells expressing TACI-Fc fusion protein are cultured and the culture supernatant is collected. The fusion protein can be extracted from the supernatant and purified using a protein A or G affinity chromatography. The levels of the secreted fusion proteins can be measured by ELISA kits.

Modification of Amino Acid and/or Polynucleotide Sequences

If desired, the subject fusion protein can be modified by any suitable process. For example, the binding affinity of the fusion protein to BLyS and/or APRIL can be increased via various methods known in the art. For example, binding characteristics can be improved by direct mutation, methods of affinity maturation, phage display, or shuffling within the nucleic acids encoding the fusion protein molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol. Bio.* 254, 392-403; Hawkins et al. (1992) *J. Mol. Bio.* 226, 889-896; or Low et al. (1996) *J. Mol. Bio,* 250, 359-368 (each of which is hereby incorporated by reference in its entirety, particularly with respect to methods of increasing the binding affinity of antibodies)). Methods known in the art include for example, Marks et al. *Bio/Technology,* 10:779-783 (1992), which describes affinity maturation by VH and VL domain shuffling; random mutagenesis of CDR and/or framework residues is described by Barbas et al. *Proc. Natl. Acad. Sci., USA* 91:3809-3813 (1994); Schier et al. *Gene,* 169:147-155 (1995); Yelton et al. *J. Immunol.,* 155: 1994-2004 (1995); Jackson et al., *J. Immunol.,* 154(7):3310-3319 (1995); and Hawkins et al, *J. Mol. Biol.,* 226:889-896 (1992).

Strategies for protein optimization are sometimes carried out using random mutagenesis. In these cases positions are chosen randomly, or amino acid changes are made using simplistic rules. For example all residues may be mutated to alanine, referred to as alanine scanning. In addition, substitution of amino acids other than those specifically exemplified or naturally present in a fusion protein of the invention are also within the scope of the present invention. For example, non-natural amino acids can be substituted for the amino acids of the fusion protein, so long as the fusion protein having the substituted amino acids retains substantially the same functional activity as the fusion protein in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a modified fusion protein of the present invention having an amino acid of one class is replaced with another amino acid of the same class fall within the scope of the subject invention so long as the modified fusion protein having the substitution still retains substantially the same functional activity (e.g., the ability to bind to the BLyS or APRIL) as the fusion protein that does not have the substitution. Polynucleotides encoding a modified fusion protein having one or more amino acid substitutions in the sequence are also within the scope of the present invention. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional fusion proteins of the invention. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a fusion protein of the present invention can be generated as described herein and tested for the presence of the desired binding characteristics using standard techniques known in the art. Thus, an ordinarily skilled artisan can readily prepare and test fragments and variants of the fusion protein of the invention and determine whether the fusion protein retains functional activity relative to the full-length or a non-variant fusion protein.

Polynucleotides and polypeptides within the scope of the subject invention can also be defined in terms of more particular identity and/or similarity ranges with those sequences of the invention specifically exemplified herein. The sequence identity will typically be greater than 75%, preferably greater than 80%, more preferably greater than 90%, and can be greater than 95%. The identity and/or similarity of a sequence can be 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6× SSPE, 5×Denhardt's solution, 0.1% SDS, 0.1 mg/ml denatured DNA. The melting temperature, Tm, is described by the following formula (Beltz et al., 1983):

$$Tm=81.5C+16.6 \log [Na+]+0.41(\% G+C)-0.61(\% \text{formamide})-600/\text{length of duplex in base pairs.}$$

Washes are typically carried out as follows:
(1) Twice at room temperature for 15 minutes in 1× SSPE, 0.1% SDS (low stringency wash).
(2) Once at Tm-20 C for 15 minutes in 0.2× SSPE, 0.1% SDS (moderate stringency wash).

Expression Constructs

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Transformation of Cells

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), retrovirus, papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Feigner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Treatment of Pathological Conditions

The invention provides pharmaceutical compositions that modulate immune responses, and are thus suitable for treating or ameliorating immune diseases, conditions or disorders in a subject, particularly diseases, conditions or disorders associated with autoimmune diseases, immunodeficiency, and B cell malignancy. In certain embodiments, it is also useful for treating or ameliorating inflammation and preventing transplant rejection in a subject.

An autoimmune disease refers to a disease, condition, or disorder that occurs when the body tissues are attacked by its own immune system. Immunodeficiency refers to a state where the immune system's ability to combat infections or infectious diseases is compromised or lost.

In certain embodiments, the subject pharmaceutical composition is useful to treat or ameliorate pathological immune conditions include, but are not limited to, rheumatoid arthritis, psoriatic arthritis, systemic lupus erythematosus, lymphocyte tumor, psoriasis, dermatitis, inflammatory bowel disease, asthma, Type-I diabetes, multiple organ injury syndrome, coronary artery disease, allergies, solid organ transplant rejections, immune complex nephritis, stiff-man syndrome, Sjogren syndrome, Hashimoto thyroiditis, juvenile (type 1) diabetes, polymyositis, scleroderma, vitiligo, pernicious anemia, glomerulonephritis, pulmonary fibrosis, leucopenia, CNS inflammatory disorders, chronic inflammatory responses, and Addison's disease.

In addition, in certain embodiments, the subject pharmaceutical composition is useful to treat or ameliorate pathological immune conditions, such as systemic myasthenia gravis, multiple sclerosis, insulin dependent diabetes mellitus, Crohn's disease, polyarticular-course juvenile rheumatoid arthritis, asthma, bronchitis, emphysema, and end stage renal failure.

In addition, the subject pharmaceutical composition is useful in certain embodiments to treat or ameliorate a disorder such as B cell neoplasms including for example B-cell lymphomas and leukemia. Chronic lymphocytic leukemia/small lymphocytic lymphoma, B cell prolymphocytic leukemia, Waldenstrom macroglobulinemia, splenic marginal zone B-cell lymphoma, hairy cell leukemia, extranodal marginal zone B-cell lymphoma of MALT type, Nodal marginal zone B-cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt lymphoma/leukemia, and lymphomatoid granulomatosis.

Therapeutic Compositions

The present invention contemplates therapeutic compositions useful for practicing the therapeutic methods described herein. The therapeutic composition can be any form of pharmaceutical format, including injectable formulations such as liquid and lyophilized injections.

The therapeutic composition may comprise isolated TACI-Fc fusion protein of the subject invention. In addition, a polynucleotide encoding the subject fusion protein may be inserted into a suitable vector and administered to a subject through gene therapy or cell therapy. Therefore, there are many methods to use the fusion proteins of the invention, not only including the subject fusion protein, but also including polynucleotides that encode the subject fusion protein. In addition, therapeutic compositions of the present invention can further comprise a physiologically tolerable carrier together with a therapeutically effective amount of fusion protein as described herein, dissolved or dispersed therein as an active ingredient. In a preferred embodiment, the therapeutic composition is not immunogenic or has reduced immunogenicity when administered to a mammal or human patient for therapeutic purposes.

The present therapeutic composition can be used in combination therapy with, e.g., antibodies, chemotherapy agents, hormones, polypeptides, and surgery. The dosing can be determined by a physician of skill in the art depending on the conditions to be treated, relevant factors, and the subject's physiological conditions.

In a specific embodiment, a therapeutically effective amount of a fusion protein is typically an amount such that when administered in a physiologically tolerable composition is sufficient to achieve a plasma concentration of from about 0.01 microgram (ug) per milliliter (mL) to about 200 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

A therapeutic composition contains the subject fusion protein typically formulated to contain an amount of at least 0.01 weight percent of antagonist per weight of total therapeutic composition. A weight percent is a ratio by weight of inhibitor to total composition. Thus, for example, 0.01 weight percent is 0.01 grams of inhibitor per 100 grams of total composition.

The invention also provides a pharmaceutical pack or kit comprising one or more containers filled with one or more of the ingredients, e.g., compound, carrier suitable for administration.

Following are examples that illustrate procedures for practicing the invention. This example should not be construed as limiting. All percentages are by weight and all solvent mixture proportions are by volume unless otherwise noted.

Example 1

Identification of Proprotein Convertase Cleavage Sites of the TACI Sequence

To identify proprotein convertase cleavage sites of native human TACI protein, the amino acid sequence of native human TACI protein is screened using the proprotein convertase (PC) artificial neural network, a computer software program that predicts potential proprotein convertase cleavage sites based on the general proprotein convertase data.

The results, as shown in FIG. 1, reveal that the TACI extracellular region includes PC cleavage sites at the $9^{th}$ amino acid residue and the $135^{th}$ amino acid residue. In addition, the $12^{th}$ amino acid residue and $120^{th}$ amino acid amino acid residue are potential PC cleavage sites.

Example 2

Construction of TACI-Fc Fusion Protein

Figure 2:
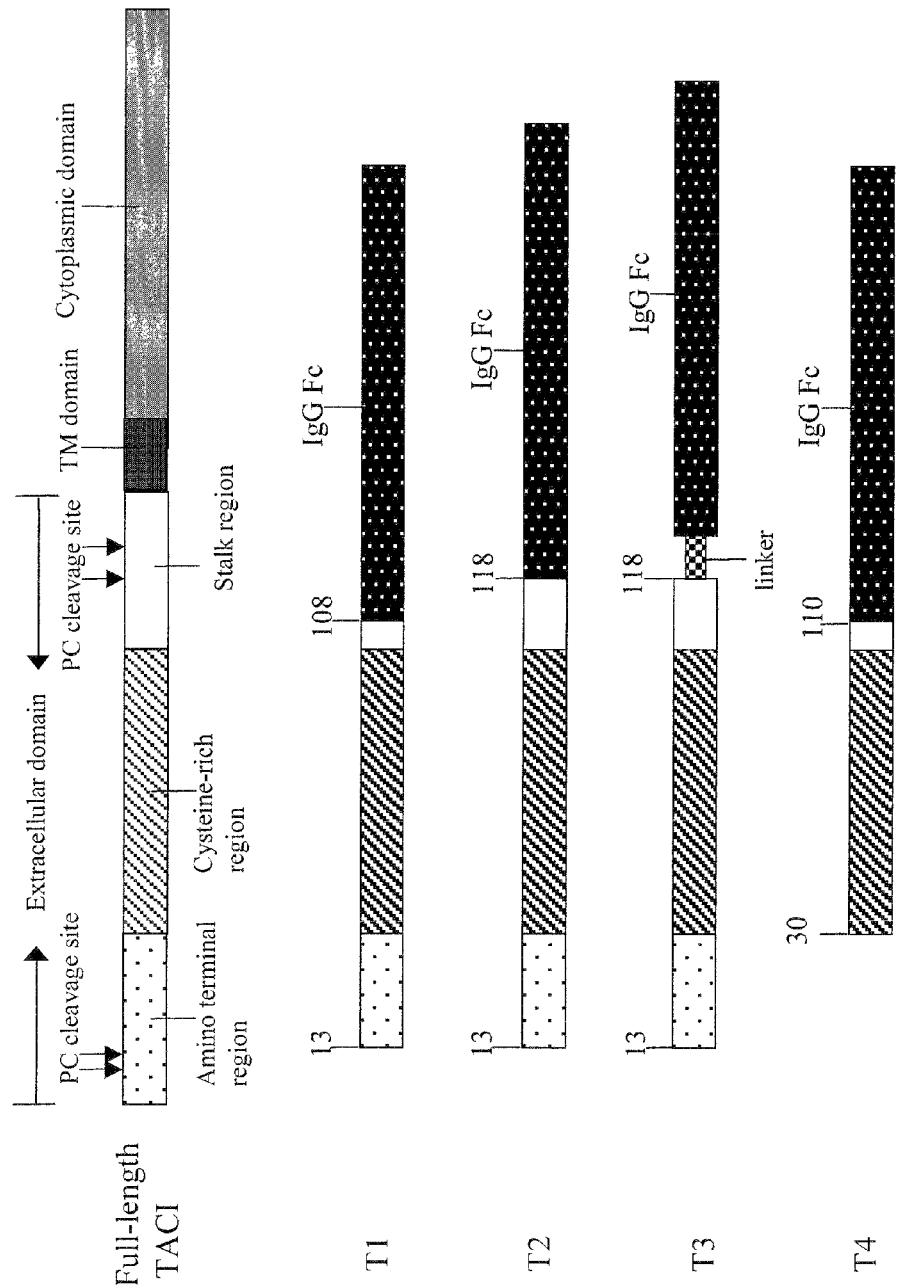
FIG. 2 is a schematic diagram of the amino acid sequence of the full length native human TACI protein and four exemplified TACI-Fc fusion proteins (T1, T2, T3 and T4).

Novel TACI-Fc fusion proteins are constructed, comprising i) a TACI polypeptide, containing an amino terminal region, a cysteine-rich region, and a stalk region; and ii) a Fc domain. Optionally, the TACI-Fc fusion protein may include a linker sequence such as 9gly. As shown in FIG. 2, exemplified TACI-Fc fusion proteins include:

T1 protein (SEQ ID NO:2), comprising i) a TACI polypeptide represented by amino acids 13 to 108 of the native human TACI protein (SEQ ID NO: 1); and ii) a Fc domain such as IgG Fc.

T2 protein (SEQ ID NO:3), comprising i) a TACI polypeptide represented by amino acids 13 to 118 of the native human TACI protein (SEQ ID NO: 1); and ii) a Fc domain such as IgG Fc.

T3 protein (SEQ ID NO:4), comprising i) a TACI polypeptide represented by amino acids 13 to 118 of the native human TACI protein (SEQ ID NO:1); ii) a linker sequence such as 9Gly, and iii) a Fc domain such as IgG Fc.

Example 3

Preparation of a TACI-Fc Fusion DNA

TACI-Fc fusion DNA can be prepared by methods illustrated as follows. First, the target TACI and Fc DNA can be generated by the following procedures. Briefly, total RNA from human peripheral blood mononuclear cells is extracted and purified using the Qiagen total RNA purification kit, and messenger RNA (mRNA) is reverse transcribed. Polymerase chain reaction (PCR) of the target gene is performed under the following conditions for 30 cycles: denaturation at 95° C., for 30 seconds, annealing at 56° C., for 45 seconds, and extension at 72° C., for 2 minutes. The immunoglobulin IgG1 Fc DNA fragment is amplified by PCR amplification under the same conditions. The PCR products of TACI DNA fragment and Fc DNA fragment are independently inserted into pCR2.1 plasmid using the TA cloning kit. The recombinant plasmid DNA is transformed into competent *E. coli* cells to replicate. After incubation, white *E. coli* colonies are selected and cultured in lysogeny broth (LB medium) overnight. Recombinant plasmid DNA is extracted and purified with a Qiagen plasmid extraction kit. Using the restriction enzymatic digestion method, it is determined that the purified TACI plasmid and Fc plasmid contain TACI and Fc DNA fragments, respectively.

The TACI and IgG Fc cDNA are joined by overlap extension PCR. The resulting TACI-Fc fusion DNA is inserted into a plasmid. The plasmid is transformed into competent *E. coli*. After positive colonies are selected and incubated overnight, the plasmid DNA is extracted and purified by a Qiagen plasmid extraction kit. Using the restriction enzyme digestion method, it is determined that the purified plasmid contains TACI and Fc-cDNA fragments.

PCR primers for exemplified fusion DNA are listed below.

Primer sequences for DNA encoding the T1 fusion protein are:

```
forward primer:
5'AGCCGTGTGGACCAGGAGGAG 3'        (SEQ ID NO: 10)
and reverse primer:
5'GAGCTTGTTCTCACAGAAGTATG 3'.     (SEQ ID NO: 110)
```

Primer sequences for DNA encoding the T2 fusion protein are:

```
forward primer:
5'AGCCGTGTGGACCAGGAGGAG 3';       (SEQ ID NO: 12)
and reverse primer:
5'GAGCTCTGGTGGAAGGTTCACTG 3".     (SEQ ID NO: 13)
```

Primer sequences for DNA encoding the T3 fusion protein are:

```
forward primer:
                                  (SEQ ID NO: 14)
5'AGCCGTGTGGACCAGGAGGAG 3"';
and reverse primer:
                                  (SEQ ID NO: 15)
5'ACCTCCACCTCCACCTCCACCTCCACCGAGCTCTGGTGGAAGGTTCAC
TGGGCTCCT 3'.
```

Fusion protein T4 (SEQ ID NO:5) comprises i) a TACI polypeptide having an amino acid sequence represented by amino acids 30 to 110 of SEQ ID NO:1; and ii) a Fc domain. T4 is distinguishable from the fusion proteins of the present invention because it does not contain a TACI amino terminal region. T4 is constructed for comparing its binding activity to BLyS with the fusion proteins of the present invention such as T1, T1 and T3. Primer sequences for DNA encoding the T4 fusion protein are:

```
forward primer:
5' GCTATGAGATCCTGCCCCGAAG 3';     (SEQ ID NO: 16)
and reverse primer:
5' TGAAGATTTGGGCTCGCTCC 3'.       (SEQ ID NO: 17)
```

Example 4

Production of TACI-Fc Fusion Proteins in Mammalian Cells

Methods for production of TACI-Fc fusion proteins in mammalian cells are illustrated as follows. Briefly, Flt-1 signal peptide DNA is linked to the 5'end of T1, T2, T3 and T4 DNA, and the Flt-1-linked T1, T2, T3 and T4 are inserted into pcDNA3.1 plasmid (Invitrogen), respectively. The TACI-Fc plasmid is purified using a high purity plasmid DNA purification kit (QIAGEN), and transfected into CHO cells using a FUGEN6 transfection kit (ROCHE), respectively.

Figure 3:
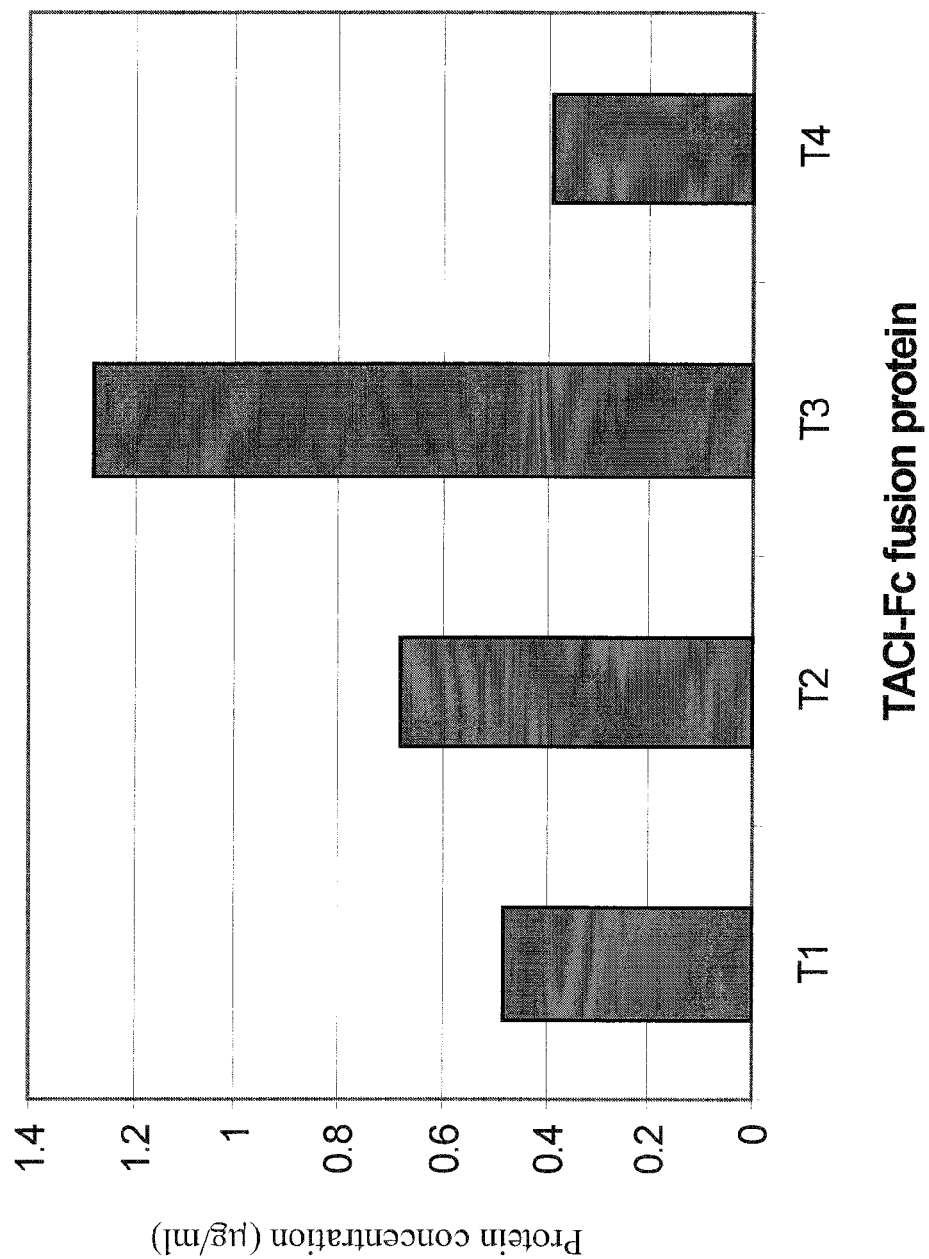
FIG. 3 shows the expression levels of the TACI-Fc fusion proteins in CHO cells.

The TACI-Fc (T1, T2, T3, and T4, respectively) fusion DNA expression level is determined using the transient transfection method. Briefly, CHO cells in Dulbecco's modified eagle medium (DMEM) containing 10% fetal calf serum are transfected with TACI-Fc plasmid DNA using a FUGEN 6 transfection reagent. After the transfected cells are cultured for three days, the supernatant is collected. TACI-Fc fusion protein expression level is determined by IgG ELISA. The results, as shown in FIG. 3, reveal that T3 is the most highly expressed protein, followed by T2, T1, and T4.

Example 5

Determination of BLYS Binding Affinity

Figure 4:
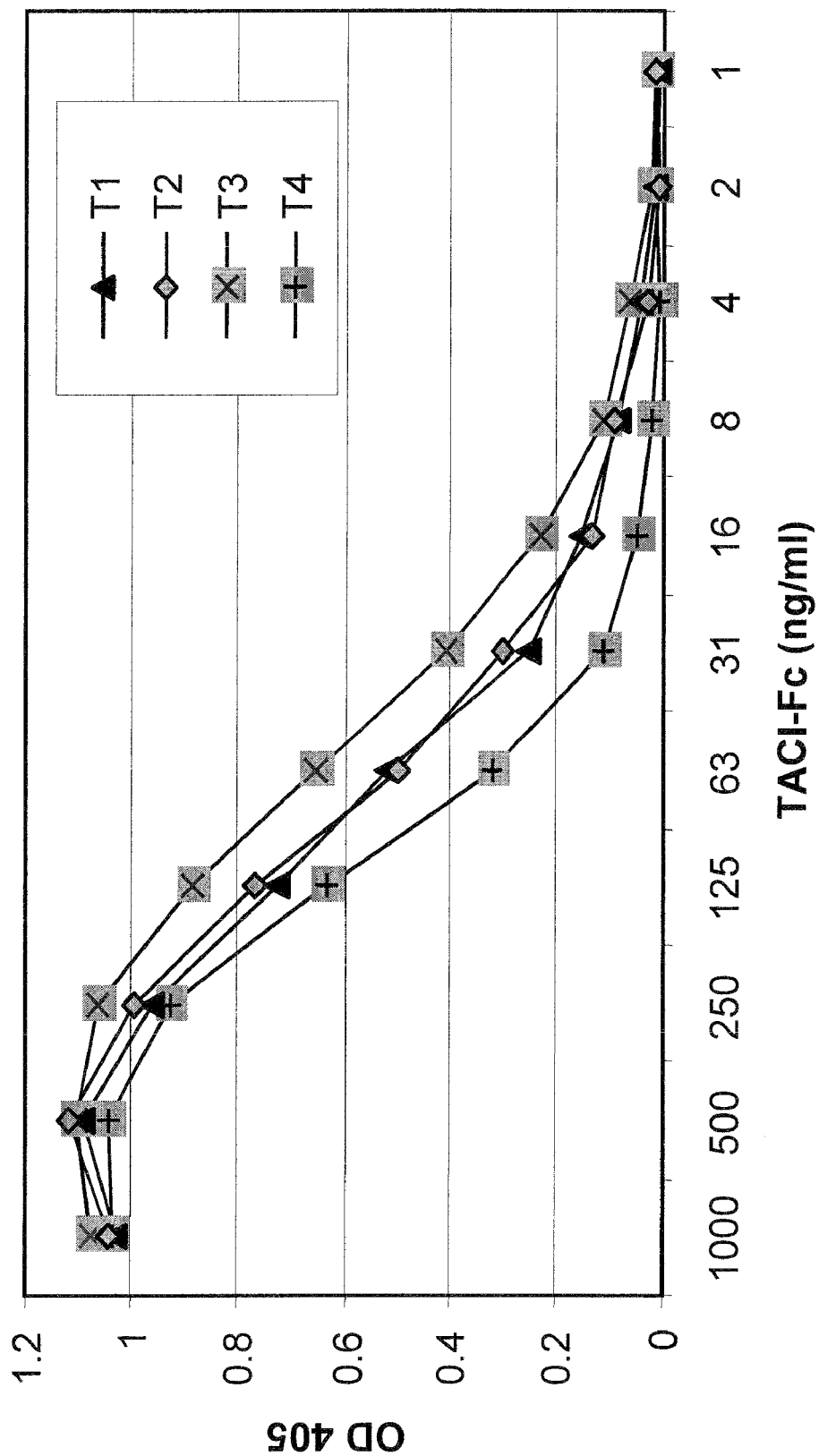
FIG. 4 shows the binding affinity of TACI-Fc fusion proteins to BLyS.

The binding affinity of TACI-Fc fusion protein to BLyS is examined in this Example. In this assay. ELISA plates are coated with recombinant BLyS (R&D Systems) protein, and blocked with 2% bovine serum albumin (BSA). Then, TACI-Fc fusion protein of various concentrations is added into in each well, followed by rabbit anti-human Ig antibody-HRP after a two-hour incubation at 37° C. The plates are incubated with peroxide substrate for color development and optical density (OD) value is read using an ELISA plate reader. The results, as shown in FIG. 4, reveal that T3 has the highest BLyS affinity, followed by T2/T1, and T4 (High OD value represents high binding affinity).

Example 6

Establishment of Expression Cell Lines that Produce TACI-Fc Fusion Proteins in High Levels To express TACI-Fc fusion proteins with high efficiency, a stably transfected CHO cell line for the TACI-Fc fusion protein is generated, followed by gene amplification to yield CHO cells with high expression levels. The TACI-Fc fusion DNA with high expression level is cloned into a plasmid that encodes dihydrofolate reductase (DHFR). The plasmid is purified using a QIAGEN plasmid purification kit, and transfected into CHO cells by electroporation. The transfected cells are plated in selection medium. The surviving colonies are picked and grown subject to methotrexate (MTX) pressure, and clones with the highest TACI-Fc fusion protein expression level are selected for production of fusion proteins on a large scale such as in the bioreactors. The TACI-Fc fusion is purified from the culture supernatant using a protein A or G affinity chromatography, and the protein concentration is determined by ELISA.

According to the procedures illustrated above, CHO cell lines with high TACI-Fc fusion productivity, for example capable of producing T3 fusion protein at 20 pg/cell per day, are obtained.

Example 7

Electrophoresis Identification of TACI-Fc Fusion Protein

Figure 5:
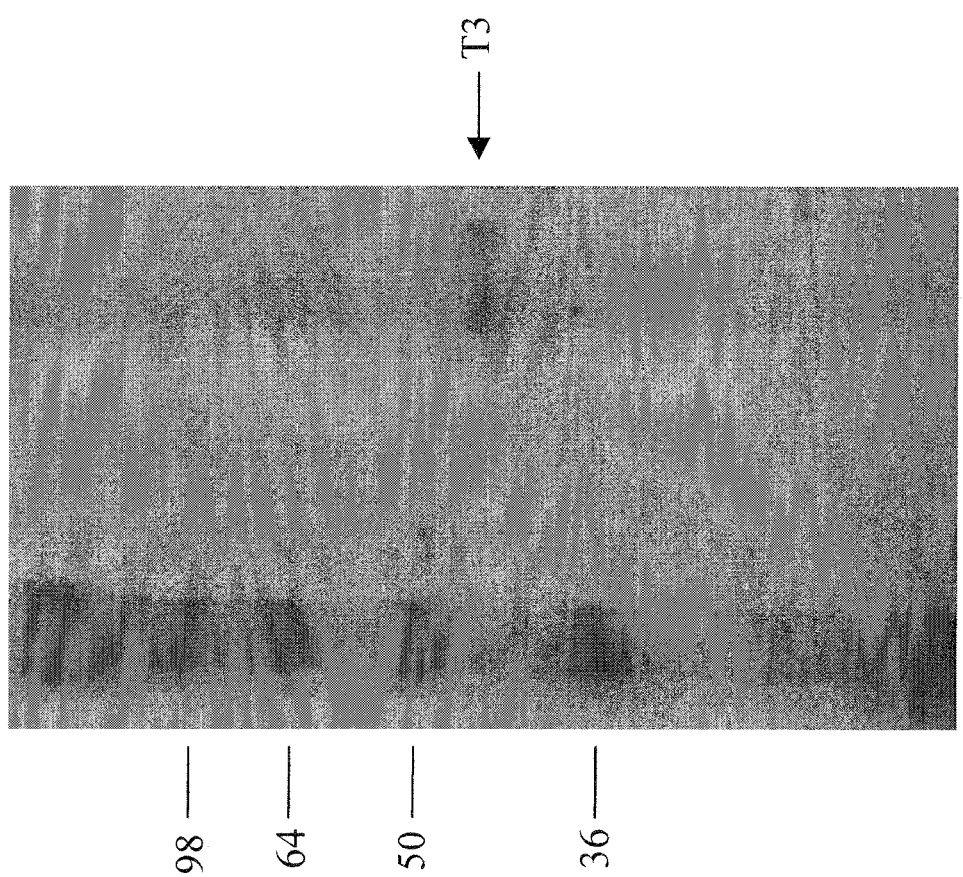
FIG. 5 shows the electrophoresis analysis of the purified T3 TACI-Fc fusion protein expressed from CHO cells.

This Example demonstrates that TACI-Fc fusion proteins of the present invention will not be cleaved or degrade during expression, thus suitable for commercial production in high expression cell lines on a large scale. Briefly, CHO cells expressing T3 fusion protein are seeded in cell culture flasks. Once cells reach confluence, the supernatant is collected to obtain purified T3 protein by protein A affinity chromatography. The purified T3 is mixed with sodium dodecyl sulfate polyacrylamide gel electrophoresis (SDS-PAGE) sample loading buffer, boiled at 100° C. for 3 minutes, and electrophoresized in polyacrylamide (PAG) gel. Following electrophoresis, the gel is stained with Coomassie Brilliant Blue 250 and destained with methanol to remove excessive stain, allowing visualization of the separated proteins. As shown in FIG. 5, only a 42 kD band is present in the gel. The size of the band is consistent with the molecular weight of T3 fusion protein after glycosylation. The N-terminal sequence of the T3 protein is further determined by using Edman method, which confirms that the recombinant TACI-Fc fusion protein expressed from CHO has an N-terminal sequence identical to that from residue 13 of SEQ ID NO:1 and no other cleaved fragments are present.

Example 8

Figure 6:
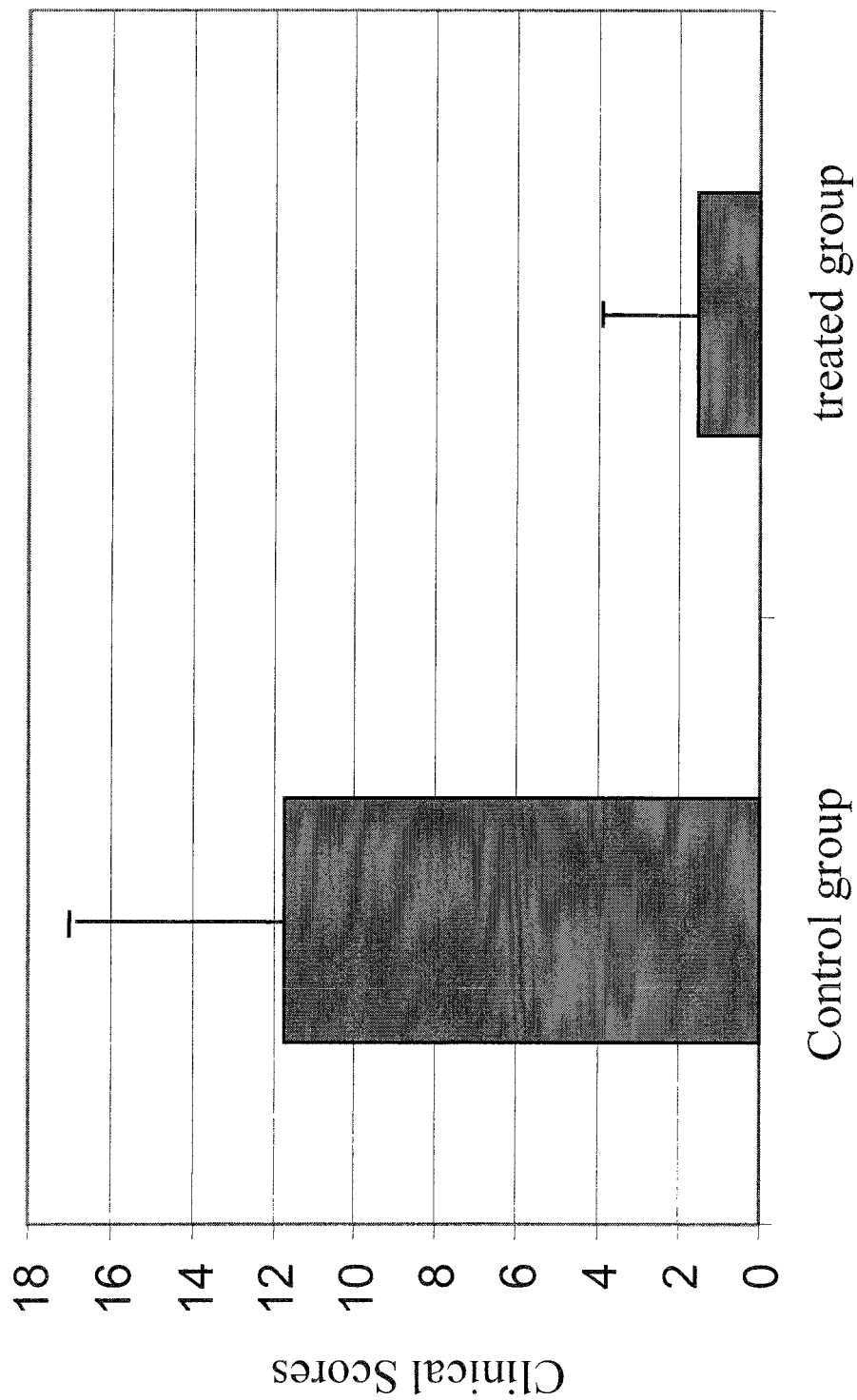
FIG. 6 shows treatment with TACI-Fc fusion protein reduces arthritis symptoms in the collagen-induced mice arthritis model.

Therapeutic Effects of the Optimized TACI-Fc Fusion Protein on Autoimmune Disease This Example illustrates that TACI-Fc fusion proteins of the present invention are suitable for treating immune conditions such as arthritis. Briefly, 20 8-week old DBA/1 mice are placed into two groups. Arthritis is induced in each group by injecting 200 μg/mouse bovine collagen type II emulsified in complete Freund' adjuvant (CFA) intracutaneously on Day 1 and 200 μg/mouse bovine collagen protein type II emulsified in incomplete Freund' adjuvant intracutaneously on Day 21. Since Day 24, each group is treated with 100 μg/mouse T3 fusion protein or IgG by subcutaneous injection three times a week. The progression of arthritis is evaluated according to standard clinical scores. The results, as shown in FIG. 6, demonstrate that the T3-treatment group exhibits a 6-fold reduction in arthritis symptoms (P<0.01).

In summary, the optimized TACI-Fc fusion proteins in the invention are uncleaved during expression, biologically active, and highly expressed from host cells, thus suitable for industrial production on large scale.

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

We claim:

1. A TACI-Fc fusion protein that comprises a TACI polypeptide that consists of amino acids 13 to 119 of SEQ ID NO:1, or a fragment thereof, that starts at any of amino acids 13 to 29 of SEQ ID NO:1, extends through, and terminates at, any of amino acids 105 to 119 of SEQ ID NO:1 and which binds to BLyS or APRIL or both, or a variant of said polypeptide or fragment thereof that has at least 90% sequence identity with said polypeptide or fragment and which binds to BLyS or APRIL or both; and wherein said fusion protein further comprises an Fc domain.

2. The TACI-Fc fusion protein, according to claim 1, wherein said variant polypeptide has at 95% sequence identity to amino acids 13 to 119 of SEQ ID NO:1 or said fragment thereof.

3. The TACI-Fc fusion protein, according to claim 1, wherein the amino acid sequence of the TACI polypeptide terminates at amino acid 108 of SEQ ID NO:1.

4. The TACI-Fc fusion protein, according to claim 1, wherein the amino acid of the TACI polypeptide terminates at amino acid 118 of SEQ ID NO:1.

5. The TACI-Fc fusion protein, according to claim 1, wherein the Fc domain is selected from the group consisting of IgG, IgM, IgD, IgE, and IgA.

6. The TACI-Fc fusion protein, according to claim 5, wherein the Fc domain is IgG1.

7. The TACI-Fc fusion protein, according to claim 1, wherein the Fc domain comprises a hinge region, a CH2 region and a CH3 region.

8. The TACI-Fc fusion protein, according to claim 1, further comprising a linker sequence that links the TACI polypeptide to the Fc domain.

9. The TACI-Fc fusion protein, according to claim 8, wherein the linker sequence is SEQ ID NO: 18.

10. The TACI-Fc fusion protein, according to claim 1, wherein the amino acid sequence of said TACI-Fc fusion protein is selected from the group consisting of SEQ ID NO:2, SEQ ID NO:3, and SEQ ID NO:4.

11. The TACI-Fc fusion protein, according to claim 1, wherein the variant of said polypeptide or fragment thereof has at least 97% sequence identity with said polypeptide or fragment, and the variant binds to BLyS or APRIL or both.

12. The TACI-Fc fusion protein, according to claim 1, wherein the TACI polypeptide consists of amino acids 13 to 119 of SEQ ID NO:1; or a fragment thereof that starts at any of amino acids 13 to 29 of SEQ ID NO:1, extends through, and terminates at, any of amino acids 105 to 119 of SEQ ID NO:1.

13. A TACI-Fc fusion protein that comprises a TACI polypeptide consisting of SEQ ID NO:1 or a fragment thereof that binds to BlyS or APRIL or both wherein said fragment comprises amino acids 30 to 104 of SEQ ID NO:1, and which has had the PC cleavage sites at amino acids 12 and 120 removed.

14. A pharmaceutical composition comprising a TACI-Fc fusion protein of claim 1 and a pharmaceutically acceptable carrier.

15. A method for recombinant production of homogeneous TACI-Fc fusion proteins, wherein said method comprises:
   i) constructing a TACI DNA fragment encoding a TACI polypeptide comprising at least a part of the amino terminal region consisting of amino acids 13-29 of SEQ ID NO:1, a cystein-rich region, and at least a part of the stalk region, wherein the TACI DNA encodes a TACI polypeptide that does not contain proprotein cleavage sites;
   ii) joining the TACI DNA fragment with a Fc DNA to obtain a TACI-Fc fusion DNA;
   iii) inserting the TACI-Fc fusion DNA into a plasmid;
   iv) transfecting host cells with the TACI-Fc fusion plasmid DNA,
   v) expressing the TACI-Fc fusion protein, and
   vi) recovering the TACI-Fc fusion protein.

* * * * *

UNITED STATES PATENT AND TRADEMARK OFFICE
CERTIFICATE OF CORRECTION

PATENT NO. : 8,193,316 B2
APPLICATION NO. : 12/638392
DATED : June 5, 2012
INVENTOR(S) : Jianmin Fang et al.

It is certified that error appears in the above-identified patent and that said Letters Patent is hereby corrected as shown below:

Column 1,
Line 30, "investigation" should read --Investigation--

Line 57, "TACT" should read --TACI--

Column 2,
Lines 66-67, "Fe domain" should read --Fc domain--

Column 5,
Line 32, "TACT" should read --TACI--

Line 57, "Fe's, the term" should read --Fc's, the term--

Column 6,
Line 1, "Fe or by" should read --Fc or by--

Column 8,
Line 11, "NSO cells" should read --NS0 cells--

Line 48, "TACT DNA" should read --TACI DNA--

Column 9,
Line 14, "TACT" should read --TACI--

Column 13,
Line 39, "Feigner et al." should read --Felgner et al.--

Column 18,
Line 12, "In this assay." should read --In this assay,--

Signed and Sealed this
Fourteenth Day of August, 2012

David J. Kappos
*Director of the United States Patent and Trademark Office*